(12) United States Patent
McNeff et al.

(10) Patent No.: US 8,043,633 B2
(45) Date of Patent: Oct. 25, 2011

(54) METHODS AND COMPOSITIONS FOR CONTROLLING MICROORGANISM POPULATIONS IN THE DIGESTIVE SYSTEM OF ANIMALS

(75) Inventors: Larry C. McNeff, Anoka, MN (US); Clayton V. McNeff, Andover, MN (US)

(73) Assignee: Sartec Corporation, Anoka, MN (US)

( * ) Notice: Subject to any disclaimer, the term of this patent is extended or adjusted under 35 U.S.C. 154(b) by 523 days.

(21) Appl. No.: 12/175,281

(22) Filed: Jul. 17, 2008

(65) Prior Publication Data

US 2008/0274211 A1 Nov. 6, 2008

Related U.S. Application Data

(62) Division of application No. 11/153,252, filed on Jun. 15, 2005, now Pat. No. 7,416,742.

(60) Provisional application No. 60/580,280, filed on Jun. 16, 2004.

(51) Int. Cl.
*A61K 33/14* (2006.01)
*A61K 36/00* (2006.01)
*A23K 1/18* (2006.01)

(52) U.S. Cl. .................. 424/662; 424/438; 424/725

(58) Field of Classification Search .................. 424/662
See application file for complete search history.

(56) References Cited

U.S. PATENT DOCUMENTS

| 6,475,527 B1 | 11/2002 | Anderson et al. |
| 6,761,911 B2 | 7/2004 | Anderson et al. |
| 7,416,742 B2 | 8/2008 | McNeff et al. |

OTHER PUBLICATIONS

Cheeke, P. R., "Actual and potential applications of *Yucca schidigera* and *Quillaja saponaria* saponins in human and animal nutrition", Proceedings of the American Society of Animal Science, 1999, 1-10.*
T R Callaway, R C Anderson, K J Genovese, T L Poole, T. J. Anderson, J. A. Byrd, L. F. Kubena and D. J. Nisbet, "Sodium chlorate supplementation reduces *E. coli* O157:H7 populations in cattle", Journal of Animal Science, 2002, 80, 1683-1689.*
K. Asres, F. Bucar, E. Knauder, V. Yardley, H. Kendrick and S. L. Croft, "In vitro Antiprotozoal Activity of Extract and Compounds from the Stem Bark of *Combretum molle*", Phytotherapy Research, 2001, 15, 613-617.*
Hristov, A. N., McAllister, T. A., Van Herk, F. H., Cheng, K. J., Newbold, C. J. and Cheeke, P. R., "Effect of *Yucca schidigera* on Ruminal Fermentation and Nutrient Digestion in Heifers", Journal of Animal Science, 1999, 77, 2554-2563.*
Anderson, R. C. "Effect of Sodium Chlorate on *Salmonella typhimurium* Concentrations in the Weaned Pig Gut", *Journal of Food Protection* 2001, vol. 64, No. 2, pp. 255-258.

Barker, John "Survival of *Escherichia coli* O157 in a soil protozoan: implications for disease", *FEMS Microbiol. Lett. 173*(2) Apr. 15, 1999, 291-295.
Boyaka, Prosper N. "Oral QS-21 Requires Early IL-4 Help for Induction of Mucosal and Systemic Immunity", *J Immunol 166*(4) 2001, 2283-2290.
Burkey, T. E. "Effect of Dietary Mannanoligosaccharide and Sodium Chlorate on the Growth Performance, Acute-Phase Response, and Bacterial Shedding of Weaned Pigs Challenged with *Salmonella enterica* Serotype Typhimurium", *J. Anim. Sci 82*(2) Feb. 2004, 397-404.
Dehority, Burk A. "Evaluation of Subsampling and Fixation Procedures Used for Counting Rumen Protozoa", *Appl. Environ. Microbiol. 48*(1) Jul. 1984,182-185.
Dumitru, Razvan "Targeting Methanopterin Biosynthesis To Inhibit Methanogenesis", *Appl. Environ. Microbiol. 69*(12) Dec. 2003, 7236-7241.
Eschenlauer, S. C. "Ammonia Production by Ruminal Microorganisms and Enumeration, Isolation, and Characterization of Bacteria Capable of Growth on Peptides and Amino Acids from the Sheep Rumen", *Appl. Environ. Microbiol. 68*(10) Oct. 2002, 4925-4931.
Fahmy, Wael G. "Effect of Defaunation and Amino Acid Supplementation on Growth and Amino Acid Balance in Sheep", Aug. 5, 1998.
Francis, George "The biological action of saponins in animal systems: a review.", *Br. J. Nutr. 88*(6) 2002, 587-605.
Goodall, S. R. "Rumensin with and without Sarsaponin for Finishing Feedlot Steers", *Col. Agr. Exp. Station No. 700* 1981.
Goodall, S. R. "Sarsaponin effects upon ruminal VFA concentrations and weight gain of feedlot cattle", *J. Anim. Sci. 49* 1979, 377-382.
Goodall, Richard S. "Sarsaponin in Beef Cattle Rations", *Beef Nutrition Research* 1978, 9-10.
Goodall, S. R. "The Effect of Sarsaponin with and without Rumensin in High-Energy Diets", *Col. Agr. Exp. Station No. 700* 1981.
Hristov, A. N. "Fermentation characteristics and ruminal ciliate protozoal populations in cattle fed medium- or high-concentrate barley-based diets", *J. Anim Sci. 79* 2001, 515-524.
King, Christopher H. "Survival of Coliforms and Bacterial Pathogens within Protozoa during Chlorination", *Appl. Environ. Microbiol. 54*(12) Dec. 1988, 3023-3033.
Klita, P. T. "Effects of alfalfa root saponins on digestive function in sheep", *J. Animal Sci. 74* 1996, 1144-1156.
Koenig, K. M. "Effects of protozoa on bacterial nitrogen recycling in the rumen", *J. Anim Sci. 78* 2000, 2431-2445.
Lila, Z. A. "Effect of Sarsaponin on Ruminal Fermentation with Particular Reference to Methane Production in Vitro", *J. Dairy Sci. 86* 2003, 3330-3336.
Lu, C. D. "Alfalfa saponins affect site and extent of nutrient digestion in ruminants", *J. Nutr. 117* 1987, 919-927.
Ly, T. M. "Ingested *Listeria monocytogenes* survive and multiply in protozoa", *J. Med. Microbiol. 33*(1) 1990, 51-54.

(Continued)

*Primary Examiner* — Johann Richter
*Assistant Examiner* — Nathan W Schlientz
(74) *Attorney, Agent, or Firm* — Pauly, DeVries, Smith & Deffner, L.L.C.

(57) ABSTRACT

The invention is related to methods and compositions for controlling microorganism populations in the digestive system of an animal. In an embodiment, the invention is a composition for reducing the bacterial load in the digestive tract of an animal including a saponin containing composition and an anti-microbial agent. Other embodiments are included herein.

6 Claims, 1 Drawing Sheet

OTHER PUBLICATIONS

Maday, John "Assault on Pathogens", *Drovers* (www.drovers.com/news_editorial.asp?pgID=676&ed_id=2499) Feb. 12, 2004.

Mendoza, G. D. "Influence of ruminal protozoa on site and extent of starch digestion and ruminal fermentation", *J. Anim Sci. 71* 1993, 1572-1578.

Navas-Camacho, Alberto "Effect of reducing the rumen ciliate protozoa population by feeding saponin-containing plants on rumen function of sheep fed on wheat straw", *Arch. Latinoam. Prod. Anim. 5*(Supp. 1) 1997, 98-101.

Oldick, B. S. "Compartmental modeling with nitrogen-15 to determine effects of degree of fat saturation on intraruminal N recycling", *J. Anim Sci. 78* 2000, 2421-2430.

Oldick, B. S. "Effects of degree of fat saturation on fiber digestion and microbial protein synthesis when diets are fed twelve times daily", *J. Anim Sci. 78* 2000, 2412-2420.

Rasmussen, Mark A. "*Escherichia coli* O157:H7 and the Rumen Environment", *E. coli O157 in Farm Animals* (*CAB International 1999*), 39-49.

Rasmussen, M. A. "Microbial Factors/Pathogenesis of Subacute Rumen Acidosis (SARA) in Cattle to Assure Food Safety", Project No. 3625-31320-001-00D, *National Animal Disease Center*, ARS/USDA Dec. 15, 2005.

Rush, Ivan "Grain Tempering Agent (SarTemp) for Corn in Finishing Rations", *Beef Cattle Report* 1993, 63-64.

Taylor, Stephanie J. "Infection of *Acanthamoeba castellanii* with *Mycobacterium bovis* and *M. bovis* BCG and Survival of *M. bovis* within the Amoebae", *Appl. Environ. Microbiol. 69*(7) Jul. 2003, 4316-4319.

Towne, Gene "Omasal Ciliated Protozoa in Cattle, Bison, and Sheep", *Appl. Environ. Microbiol. 56*(2) Feb. 1990, 409-412.

Wallace, R. J. "Influence of *Yucca shidigera* Extract on Ruminal Ammonia Concentrations and Ruminal Microorganisms", *Appl. Environ. Microbiol. 60*(6) Jun. 1994, 1762-1767.

Wang, Y. "Effect of steroidal saponin from *Yucca schidigera* extract on ruminal microbes", *J. Appl. Microbiol. 88*(5) 2000, 887-896.

Wang, Y. "Effects of *Yucca schidigera* extract on fermentation and degradation of steroidal sponins in the rumen simulation technique (RUSITEC)", *Animal Feed Sci. Technol. 74* 1998, 143-153.

Wilson, R. C. "Effects of *Yucca shidigera* Extract and Soluble Protein on Performance of Cows and Concentrations of Urea Nitrogen in Plasma and Milk", *J. Dairy Sci. 81* 1998, 1022-1027.

Zinn, R. A. "Influence of tempering on the feeding value of rolled corn in finishing diets for feedlot cattle", *J. Anim Sci. 76* 1998, 2239-2246.

\* cited by examiner

METHODS AND COMPOSITIONS FOR CONTROLLING MICROORGANISM POPULATIONS IN THE DIGESTIVE SYSTEM OF ANIMALS

This application is a divisional application of prior application Ser. No. 11/153,252, filed Jun. 15, 2005, which claims the benefit of U.S. Provisional Application No. 60/580,280, filed Jun. 16, 2004, the contents of all of which are herein incorporated by reference.

FIELD OF THE INVENTION

The invention is related to methods and compositions for controlling microorganism populations in the digestive system. More specifically, the invention is related to methods and compositions including saponins for controlling microorganism populations, such as pathogenic bacteria populations, in the digestive system of animals.

BACKGROUND OF THE INVENTION

Food borne bacterial disease associated with the consumption of meat and poultry products results in 5,000,000 illnesses and 4,000 deaths per year (United States Department of Agriculture Food Safety Inspection Service Control of Pathogenic and Spoilage Bacteria on Red Meat (404497)). For example, eating contaminated ground beef that has not been cooked sufficiently to kill *E. coli* can result in *E. coli* infection. The Center for Disease Control (CDC) reports that 73,000 illnesses and 61 deaths occur in the United States each year specifically from *E. coli* 0157: H7.

Beef, sheep, and ruminants in general have a symbiotic relationship with bacteria that live in their fore stomach or rumen. Most of these microorganisms are harmless to people and are helpful to their hosts. However, *E. coli* 0157:H7, *Salmonella typhimurium*, and some *Clostridia* species are pathogenic and can cause illness. These microorganisms are shed in the manure of animals and are easily introduced into ground meats during processing.

In addition to the human health threat, the red meat industry suffers economic hardship each year due to recalls of meat contaminated with pathogenic organisms. For example, *E. coli* 0157:H7 based recalls of food products are common and frequently make the national news in the United States alone. Presently, the United States Department of Agriculture (USDA) and the beef processing industry have implemented a program to decontaminate carcasses post-harvesting in order to reduce the incidence contamination food products and therefore reduce the incidence of food borne bacterial disease. However, many cases of food borne bacterial disease still arise.

Therefore, a need exists for methods and compositions that will help reduce the incidence of contamination of food products.

SUMMARY OF THE INVENTION

The invention is related to methods and compositions for controlling microorganism populations in the digestive system of an animal. In an embodiment, the invention is a method for reducing protozoa populations in the digestive system of an animal including administering an effective amount of a saponin containing composition to the animal, and administering an effective amount of an anti-microbial agent to the animal. In an embodiment, the invention is a composition for reducing the bacterial load in the digestive tract of an animal including a saponin containing composition and an anti-microbial agent. In an embodiment, the invention is a method for reducing the bacterial load in the digestive system of an animal including administering an effective amount of a saponin containing composition to the animal.

The above summary of the present invention is not intended to describe each discussed embodiment of the present invention. This is the purpose of the detailed description that follows.

DETAILED DESCRIPTION OF THE INVENTION

Figure 1:
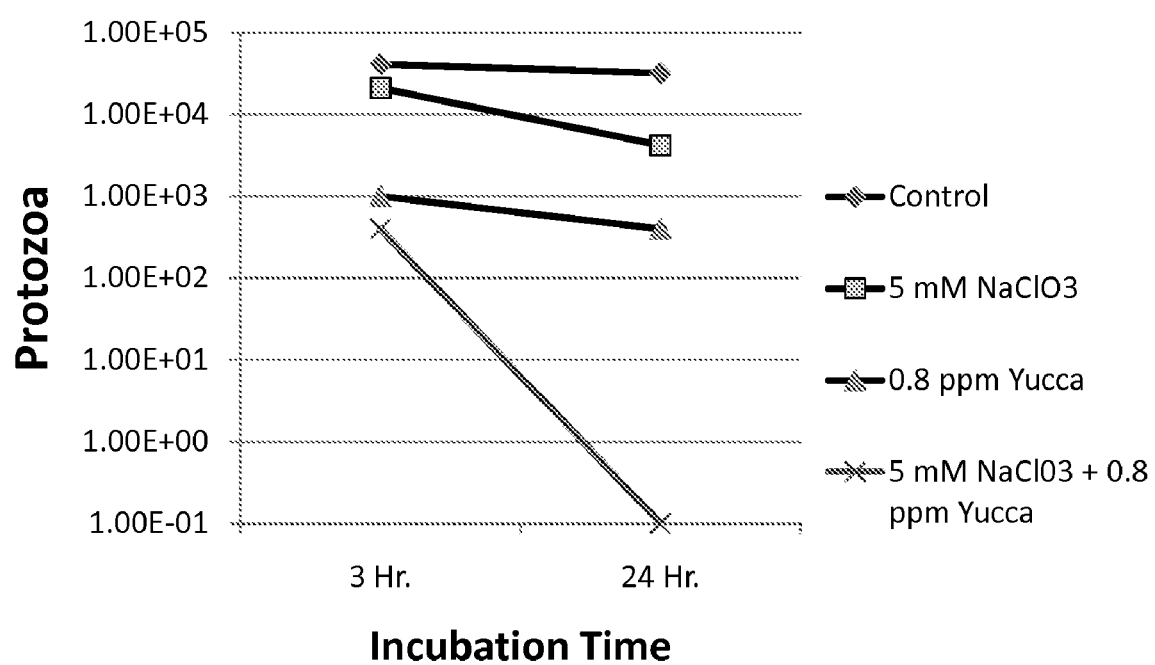
FIG. 1 is a chart showing numbers of protozoa with different treatments and incubation times.

Pathogenic microorganisms are shed in the manure of animals and are easily introduced into ground meats during processing. Therefore, one approach to reducing instances of contamination is to control or reduce the amount of pathogenic microorganisms in the manure of animals prior to slaughter.

Sodium chlorate can be administered to animals pre-slaughter to reduce food borne pathogens as discussed in US patent application publication 20030039703, "Use of chlorate ion or preparations thereof for reduction of food borne pathogens", herein incorporated by reference.

*E. coli* 0157:H7, *Salmonella typhimurium*, and some *Clostridia* species in the digestive tract are killed when sodium chlorate is fed to animals at low levels or applied to the surface of animals including beef cattle, sheep and swine prior to slaughter. Bacteria that can anaerobically respire on nitrate (i.e. *E. coli* and *Salmonella typhimurium*) can co-metabolically reduce chlorate to chlorite. The chlorite then kills the bacteria.

Other symbiotic microorganisms in the rumen are not significantly affected by sodium chlorate. Other anaerobic bacteria living in the rumen that do not convert nitrate to nitrite are compatible with the chlorate because they never generate the lethal chlorite species. The health of the animals is also not adversely affected.

Among the many different forms of microorganisms inhabiting the fore stomach of ruminants are bacteria, archaea, fungi, and protozoa. It has been reported in research publications that protozoa harbor pathogenic bacteria (*Applied and Environmental Microbiology*, 2003, 69:4316-4319; *The Journal of Medical Microbiology*, 33:51-54; and *FEMS Microbiology Letters*, 1999, 173:291-295).

Protozoa are eukaryotes, one celled animals that are found in many parts of the ecosystem including soil, ponds, the digestive tract of insects (cockroaches) and the fore stomach of ruminants. Protozoa, thought to be the most ancient form of animals, consume bacteria (thought to be the most ancient form of life) as food. After the outbreak of Legionnaires Disease, killing a number of people in Philadelphia, Pa. in the 1970's, it was discovered that the causative agent was a strain of *Legionella pneumophila*, a pneumonia causing bacteria that had survived as intracellular guests within in the protozoa thought to be living the cooling system of the building in which the Legionnaires gathered. Similarly, it has been reported that *Salmonella, Mycobacterium bovis, Listeria monoytogenes* and *E. coli* 0157:H7 can survive intracellularly in soil protozoa. Even as these soil protozoa become encysted in response to poor environmental conditions, the intracellular pathogens remain viable. In addition, studies have reported that intracellular pathogens can be resistant to bactericidal treatments such as chlorine (*Appl. Environ. Microbiol.*, 1988, 54(12):3023-33).

Thus, free-living protozoa are believed to be able to act as a "Trojan Horse" and carry pathogenic endosymbiants. In this manner, the protozoa can act as a life-preserving capsule for the pathogen. Recent studies suggest that some *Salmonella*, when ingested by rumen protozoa, developed the ability to resist the digestive processes of the protozoa and remain viable. Further, it was reported the pathogen can become more virulent after living within the protozoa in comparison to counterparts that have not lived inside the protozoa.

Rumen microorganisms are swept from the fore-stomach of the ruminant animal into the lower digestive tract. In the lower digestive tract, microorganisms are digested and provide nutrients for the host ruminant. Protozoa are moved more slowly from the rumen of the animal because of their ability to cling to the larger undigested feedstuffs and to the rumen walls. Their turnover rate is much slower and this phenomenon allows the intracellular pathogens to sustain themselves in the rumen. The rumen is then a reservoir for the pathogens. As some of the protozoa are swept into the lower digestive system of the ruminant, the protozoa are digested releasing the more virulent pathogens. The pathogens that have developed a resistance to the digestive processes survive and are shed in the manure of the host animal.

Saponins can lyse protozoa, thereby killing them. By way of example, a *yucca*-based extract composition, containing saponins, can reduce protozoal counts in the rumen of an animal. In an embodiment of the invention, a saponin containing composition can produce an 11-14% reduction in protozoal counts in the rumen. Saponins are naturally occurring glycosides found in a wide variety of different plant species. Chemically they are glycosides that have both an aglycone (sapogenin) and a carbohydrate portion of the molecule that makes them natural plant soaps. The sugar portion of the saponin may be attached to either a treiterpene or steroidal aglycone moiety. The complexity of the saponins is derived primarily from the carbohydrate portion of the molecule, due to the different types, number and anomeric configuration possibility of the attached oligosaccharide. There are three main classes of saponins, namely triterpense, steroid and steroid alkaloid. A more complete description of saponins can be found in Hostettmann and Marston (1995).

It has been discovered that there is a synergistic effect between saponins and anti-microbial agents, such as sodium chlorate, on reduction of microorganism populations. Specifically, as shown in example 3 below, a saponin containing composition in combination with an anti-microbial agent can reduce protozoa populations more than either the saponin containing composition alone or the anti-microbial agent alone.

While not intending to be bound by theory, it is believed that saponins can enhance the effects of other agents, such as sodium chlorate, designed to reduce pathogenic bacterial burden because the pathogens that are otherwise protected inside the protozoa are made available to the lethality of the sodium chlorate. Sodium chlorate must come into intimate contact with the pathogen in order for the pathogen to convert it to chlorite thus killing the bacterium. As long as the pathogen is protected inside the protozoa it can survive even in the presence of sodium chlorate. It is believed that the complete removal of *E. coli* from the digestive system is not possible without administration of saponin containing compositions because the protozoa harboring *E. coli* provides a safety shield. Thus, intracellular *E. coli* 0157:H7 are afforded a continuing opportunity to re-infect the ruminant. However, saponins lyse the protozoa breaking down the protection of the protozoan cell membrane providing access to the intracellular pathogens for the sodium chlorate. Therefore, it is believed that complete removal of the pathogen from the digestive tract can be achieved by administering sodium chlorate to the animal in the presence of a sufficient amount of saponin containing agents.

Sodium chlorate studies report more pathogen survival in the rumen than in the colon of the ruminant. This finding would be in keeping with the fact that more protozoa live in the rumen than in the colon of the animal. The fact that saponins destroy protozoa, which can harbor pathogens such as *E. coli* and *salmonella*, helps in the clearance of these pathogens from an animal even without the use of another agent such as sodium chlorate. In an embodiment, the invention is directed to a method for reducing pathogenic bacterial burden in the digestive tract of an animal comprising administering a saponin containing composition.

The methods and compositions of the invention can be used for the treatment of meat-producing animals, including bovine, fowl, porcine, ovine, and equine species. By way of example, the methods and compositions of the invention can be used for the treatment of cattle, chickens, turkeys, ducks, quail, geese, pigs, and sheep. In an embodiment, the methods and compositions of the invention can be used for the treatment of ruminants.

Saponin Containing Compositions:

As discussed above, saponins are naturally occurring glycosides found in a wide variety of different plant species. Chemically they are glycosides that have both an aglycone (sapogenin) and a carbohydrate portion of the molecule that makes them natural plant soaps.

Saponin containing compositions in accordance with the invention may not be effective if they do not contain a sufficient amount of saponins. In an embodiment, the saponin containing composition used in accordance with the invention comprises at least 0.5% by weight saponins. In an embodiment, the saponin containing composition used in accordance with the invention comprises at least 1.0% by weight saponins. In a particular embodiment, the saponin containing composition used in accordance with the invention comprises at least 2.0% by weight saponins.

As different plant types contain varying concentrations of saponins, only extracts from some types of plants may be effective in accordance with the invention. By way of example, saponins useful in the present invention may also be extracted in sufficient concentrations from plants of the family: Amaryllidaccae, genus: *Agave*, which grows extensively in the southwestern United States and in Mexico. Saponins useful in the present invention may also be extracted in sufficient concentrations from plants of the family: Lillaecae, genus: *Yucca*, as well as from *Quillaja saponaria* bark. Saponins may be extracted from plant materials in accordance with techniques well-known by those of skill in the art.

An exemplary liquid composition containing saponins is sold under the trademark SARTEMP® by SarTec Corporation of Anoka, Minn. It can prepared by blending an aqueous extract of the plants of the family: Lillaecae, genus: *Yucca*, or other appropriate *Yucca* plants containing 10% solids with antifreeze agents such as calcium chloride, propylene glycol, and the like, to depress the freezing point to −30° F. The final concentration of *Yucca* soluble solids is 8.25%. The physical and chemical data of SARTEMP® are as follows: Bulk density—10.4 lbs. per gallon; Color—Dark brown; Freezing Point—−30° F.; Saponin—at least 390 grams per gallon (3 grams per ounce); pH—5.5-6.0; Total solids—33%; Water—67%.

Other exemplary liquid solutions containing saponins are sold under the trademarks SARSTART®, SARSTART PRO®, and SARSTART PLUS®. These drench products can be administered orally through the use of a drench gun. These liquid solutions may comprise a variety of components. By way of example, SARSTART PLUS® can contain the following ingredients: Water, Propylene Glycol, *Yucca Schidigera* Extract, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), Naturally Occurring Organisms, Dried Egg Solids, Dried Casein, and Dried Whey. The physical and chemical characteristics of SARSTART PLUS® are as follows: Boiling Point: 240 F; Specific Gravity: 1; Melting Point: −20 F; Solubility in Water: Miscible; Appearance and Odor: Dark brown liquid with a mild odor and a slightly acid taste.

The typical saponin content that naturally occurs in *yucca* plants is from 0.1-2% saponins by weight. *Yucca* extracts can be derived by extracting *yucca* powder with an aqueous solution that may or may not contain some fraction of organic solvent such as methanol, ethanol, propanol, butanol, or the like. Commercially available *Yucca* extracts can have a total solids content usually in the range from 5-50%. The saponin content of a typical 50 brix (50% solids by weight) *yucca* extract is usually in the range of about 1-2% saponins by weight as measured by HPLC analysis. Exemplary drench products containing saponins, may comprise from between 1 to 95% 50 brix *yucca* extract. The dosage target for ruminants is enough to reduce or completely eliminate (defaunate) protozoans in the rumen. Other defaunation agents (such as sunflower seed oil with high linoleic acid content, groundnut oil, or ionophores such as Laidlomycin, Lasalocid, Maduramicin, Monensin, Narason, Salinomycin and Semduramicin) may also be used in conjunction with saponins.

Saponin containing compositions can also be formulated as dry powder. Such dry formulations are available commercially (SARSTART D®, SARSTART DSC®, SarTec Corporation, Anoka, Minn.). Dry powder formulations of saponin containing compositions may be added to the feed ration via a micro-ingredient machine or added to a feed mix truck and mixed thoroughly to assure even distribution in the feed. By way of example, a dry formulation (such as SARSTART D®, SARSTART DSC®) may be added at a rate of 0.25 gram to 10 grams per head per day rate.

Dosing of Saponin Containing Compositions:

Saponin containing compositions in accordance with the invention may be in liquid or dry forms. By way of example, a saponin containing plant extract may be dried into a powder form. In this form, the saponin containing composition may be administered to an animal as a pill or bolus, or mixed in with other components such as a feed ration. Saponin containing plant extract may also be in a solution with an amount of a carrier liquid such as water. In this form, the saponin containing composition may be administered to an animal as a liquid drench.

Saponin containing compositions may be administered to an animal as a single dose. Saponin containing compositions may also be administered to an animal in multiple doses. For example, an animal may receive an initial dose and then receive subsequent maintenance doses in lesser amounts. An animal may receive multiple doses of a saponin containing composition in one day, or may receive multiple doses over multiple days.

In some embodiments, an animal may receive initial doses of a saponin containing composition as a calf and then may receive maintenance doses throughout its life. In this manner, whole herds or groups of animals may be kept free of pathogenic organisms so as to minimize any opportunity for members of the herd or group to become re-infected. However, in some instances, continual use of saponin containing compositions may not be economically efficient. In an embodiment, a saponin containing composition is administered to an animal less than 130 days before the animal is slaughtered. In an embodiment, a saponin containing composition is administered to an animal less than 80 days before the animal is slaughtered. In an embodiment, a saponin containing composition is administered to an animal less than 30 days before the animal is slaughtered. In a particular embodiment, a saponin containing composition is administered to an animal less than 5 days before the animal is slaughtered. In an embodiment, a saponin containing composition is administered to an animal from between 130 and 5 days before the animal is slaughtered.

In some embodiments, a saponin containing composition may be administered even closer to the time of slaughter. By way of example, a saponin containing composition may be administered within about 96 hours, or within about 48 hours, prior to slaughter.

Animals may be treated with a saponin containing composition in an amount that is effective to reduce or eliminate pathogenic microorganisms from the digestive tract of the animal in comparison to an untreated control animal. In an embodiment, the amount of saponins in a dose of a saponin containing composition is at least about 5 milligrams. In an embodiment, the amount of saponins in a dose of a saponin containing composition is less than about 10 grams. In an embodiment, the amount of saponins in a dose of a saponin containing composition is about 5 mg to 10 grams.

Anti-Microbial Co-Agents:

Saponin containing compositions may be administered to animals alone or in combination with anti-microbial co-agents. Suitable anti-microbial co-agents include compounds of the formula $X_m(ClO_3)_n$, wherein X is a cationic moiety and m and n are independently selected from integers necessary to provide a net valency to the compound of 0, and which compounds release free chlorate ion ($ClO_3^-$) while in solution. By way of example, a saponin containing composition may be administered with an agent containing a chlorate group (salts of chloric acid), such as sodium chlorate, potassium chlorate, and the like. In an embodiment, a saponin containing composition is administered in combination with sodium chlorate. Other anti-microbial agents that can administered in combination with a saponin containing composition include antibiotics (such as neomycin and the like), and other chlorine containing compounds. Administration of the saponin containing compositions may be at the same time as administration of an anti-microbial agent or at a different time. In an embodiment, a saponin containing composition is administered at the same time as an anti-microbial agent. In an embodiment, a saponin containing composition is administered at least one hour before an anti-microbial agent is administered.

The present invention may be better understood with reference to the following examples. These examples are intended to be representative of specific embodiments of the invention, and are not intended as limiting the scope of the invention.

EXAMPLES

Example 1

Effects of a Saponin Containing Extract on Protozoal Counts in Cattle

Four crossbred yearling cattle were selected as subjects. The cattle weighed an average of 725 lbs at the time of surgery. Rumen fistulas were installed and 4" cannulas were utilized to seal the fistula. The cattle were maintained on a forage ration for the duration of the study. The ration (grass hay; 10.5% CP, 55% NDF) was fed for ad libitum access.

The preliminary phase involved establishment of baseline protozoal numbers. On day 0, rumen evacuations were done on each steer to estimate rumen volume. Following evacuation, samples were taken on each of seven consecutive days to determine day-to-day variation. Samples were collected each day between 0800 and 0900 hours and processed according to the methods of Dehority, 1984, *Appl. Environ. Micro.*, 48:182-185. Data for the preliminary phase are shown in Table 1 below.

TABLE 1

Preliminary Phase (baseline)

| Steer # | Volume (L) | Protozoal Counts ($10^4$/ml) | Total Protozoa ($\times 10^9$) |
|---|---|---|---|
| 1 | 61.4 | 35.5 ± 6.4 | 21.8 |
| 2 | 54.4 | 26.9 ± 6.9 | 14.6 |
| 3 | 50.9 | 49.2 ± 6.5 | 25.0 |
| 4 | 46.8 | 44.4 ± 5.0 | 20.8 |
| mean | 53.4 | 39.0 + 6.2 | 20.6 |

The experimental phase involved dosing the cattle with a saponin-containing composition to test the hypothesis that the composition exhibits anti-protozoal activity. Two steers were chosen randomly (#1 and #4) to receive the experimental treatment, which consisted of 50 cc of a saponin-containing composition (SarStart® Plus, SarTec, Anoka, Minn.). The two remaining steers (#2 and #3) received a control treatment, which consisted of 50 cc of isotonic saline. Steers were dosed at 0700 hours on a Monday and sampled at 12, 24, 48, 72, 96, and 108 hours later. Data for the experimental phase are shown in Table 2 below.

TABLE 2

Treatment Phase

| Steer # | Mean Baseline Count ($\times 10^4$) | Mean Baseline Total Protozoa ($\times 10^9$) | Mean Treated Count ($\times 10^4$) | Mean Treated Total Protozoa ($\times 10^9$) | % Change in Counts | % Change in Total |
|---|---|---|---|---|---|---|
| 1 | 35.5 | 21.8 | 31.5 | 19.3 | −11.3 | −11.5 |
| 2 (control) | 26.9 | 14.6 | 27.3 | 14.9 | +1.0 | +2.0 |
| 3 (control) | 49.2 | 25.0 | 50.4 | 25.7 | +1.0 | +2.8 |
| 4 | 44.4 | 20.8 | 38.3 | 17.9 | −13.7 | −14.0 |

Treated steers 1 and 4 showed decreases in total protozoa of 11.5% and 14.0% respectively while the untreated control steers 2 and 3 showed increases in total protozoa of 2.0% and 2.8% respectively. The data show that administration of a saponin containing composition resulted in a significant reduction in protozoal counts in the rumen in vivo.

Example 2

Dose Escalation Effects of a Saponin Containing Extract on Protozoal Populations in Cattle Two crossbred yearling cattle were selected as subjects for a dose escalation experiment. Rumen fistulas were installed and 4" cannulas were utilized to seal the fistula. The cattle were maintained on a forage ration for the duration of the study. The ration (grass hay; 10.5% CP, 55% NDF) was fed for ad libitum access.

The preliminary phase involved establishment of baseline protozoal numbers. On day −2, rumen evacuations were done on each steer to estimate rumen volume. Following evacuation, samples were taken on two consecutive days (days −2 and −1) to determine day-to-day variation. Samples were collected each day between 0800 hours and 0900 hours and processed according to the methods of Dehority (1984). Data for the preliminary phase are shown in Table 3.

TABLE 3

Preliminary Phase (baseline)

| Steer # | Volume (L) | Protozoal Counts ($10^4$/ml) | Total Protozoa ($\times 10^{10}$) |
|---|---|---|---|
| 1 | 53.4 | 45.6 ± 7.1 | 2.4 |
| 2 | 56.0 | 53.1 ± 9.0 | 3.0 |
| mean | 54.7 | 49.4 + 8.0 | 2.6 |

The experimental phase involved dosing the cattle with increasing doses of a saponin containing composition to determine the effect on antiprotozoal activity. Steers were subjected to the treatment and sampling protocol shown in Table 4. On Day 1 the cattle received a 50 cc of a saponin-containing composition (SarStart® Plus, SarTec, Anoka, Minn.), on day 5 the cattle received a 100 cc dose of the saponin-containing composition, and on day 9 the cattle received a 500 cc dose of the saponin-containing composition.

TABLE 4

Treatment and Sampling Protocol

| Day 1 | 1x dose |
| Day 2 | Sampled for Protozoa |
| Day 5 | 2x dose |
| Day 6 | Sampled for Protozoa |
| Day 9 | 10x dose |
| Day 10 | Sampled for Protozoa |

Data for the experimental phase are shown in Table 5 below.

TABLE 5

| Steer # | Baseline Count (×10⁴) | 1X Treatment Count | % Change | 2X Treatment Count | % Change | 10X Treatment Count | % Change |
|---|---|---|---|---|---|---|---|
| | | | Treatment Phase | | | | |
| 1 | 45.6 | 44.9 | (−1.5) | 40.6 | (−10.9) | 31.1 | (−31.7) |
| 2 | 53.1 | 48.2 | (−9.2) | 42.9 | (−19.2) | 34.2 | (−35.5) |
| Mean | 49.4 | 46.6 | (−5.5) | 41.8 | (−15.2) | 32.7 | (−33.7) |

The data show a dose dependent response for reduction in protozoal counts in the rumen in vivo.

Example 3

Synergistic Effects of a Saponin Containing Composition Along with an Antimicrobial Agent on Protozoal Populations Rumen fluid was collected from a donor cow. The rumen fluid was diluted 1:2 with a buffer and the protozoa were allowed to sediment. The protozoa were collected and then resuspended in a volume equal to $\frac{1}{6}^{th}$ of the previous volume. A log-phase culture of *Salmonella* (SL1344) was added at a MOI (multiplicity of infection) of 100. The protozoa were allowed to feed for an hour. The protozoa/*Salmonella* suspension was then aliquoted into treatment vessels and incubated for either three hours or twenty-four hours. The treatment groups were as follows: 1. 0.2% starch; 2. 0.2% starch+5 mM NaClO₃; 3. 0.2% starch+0.8 ppm *Yucca* extract; 4. 0.2% starch+5 mM NaClO₃+0.8 ppm *Yucca* extract. Protozoa were then counted. The results are shown in Table 6 below. The results are also shown in FIG. 1.

TABLE 6

| Incubation Times | Group 1: No Treatment | Group 2: 5 mM NaClO₃ | Group 3: .8 ppm Yucca | Group 4: .8 ppm Yucca Extract & 5 mM NaClO₃ |
|---|---|---|---|---|
| 3 Hr. | 4.12E+04 | 2.10E+04 | 1.00E+03 | 4.00E+02 |
| 24 Hr. | 3.20E+04 | 4.20E+03 | 4.00E+02 | 0.00E+00 |

The data show that 0.8 ppm *Yucca* extract in combination with 5 mM NaClO₃ (treatment group 4) reduced protozoal counts more significantly than either 5 mM NaClO₃ alone (treatment group 2) or 0.8 ppm *Yucca* extract alone (treatment group 3).

SPECIFIC EMBODIMENTS OF THE INVENTION

In an embodiment, the invention includes a composition for reducing the bacterial load in the digestive tract of an animal including a saponin containing composition and an anti-microbial agent. In an embodiment, the saponin containing composition includes *Yucca, Agave*, or *Quillaja* extract. In an embodiment, the saponin containing composition can include *Yucca* extract. In an embodiment, the saponin containing composition can include at least 0.5% by weight of saponins. In an embodiment, the saponin containing composition can include at least 2.0% by weight of saponins. In an embodiment, the anti-microbial agent is selected from the group consisting of sodium chlorate and potassium chlorate. In an embodiment, the anti-microbial agent contains a chlorate group. In an embodiment, the anti-microbial agent is sodium chlorate.

In an embodiment, the invention includes a method for reducing the bacterial load in the digestive system of an animal including administering an effective amount of a saponin containing composition to the animal. In an embodiment, the pathogenic bacteria can include as least one of *E. coli, S. typhimurium*, and *Clostridia* species. In an embodiment, the pathogenic bacteria is *E. coli* 0157:H7. In an embodiment, the animal is selected from the group consisting of cows, sheep, goats, pigs, and chickens. In an embodiment, the animal is a ruminant. In an embodiment, the animal is *Bos taurus*. In an embodiment, the saponin containing composition includes a plant extract. In an embodiment, the saponin containing composition can include *Yucca, Agave*, or *Quillaja* extract. In an embodiment, the saponin containing composition can include *Yucca* extract. In an embodiment, the saponin containing composition can include at least 0.5% by weight of saponins. In an embodiment, the saponin containing composition can include at least 2.0% by weight of saponins. In an embodiment, the method includes administering an effective amount of an antimicrobial agent to the animal.

In an embodiment, the invention includes method for reducing the pathogenic bacteria populations in the feces of an animal including administering an effective amount of a saponin containing composition to the animal. In an embodiment, the pathogenic bacteria is at least one of *E. coli, S. typhimurium*, and *Clostridia* species. In an embodiment, the pathogenic bacteria comprises *E. coli* 0157:H7. In an embodiment, the animal is selected from the group consisting of cows, sheep, goats, pigs, and chickens. In an embodiment, the animal is a ruminant. In an embodiment, the animal is *Bos taurus*. In an embodiment, the saponin containing composition includes a plant extract. In an embodiment, the saponin containing composition includes *Yucca, Agave*, or *Quillaja* extract. In an embodiment, the saponin containing composition includes *Yucca* extract. In an embodiment, the saponin containing composition includes at least 0.5% by weight of saponins. In an embodiment, the saponin containing composition includes at least 2.0% by weight of saponins. In an embodiment, the method further includes administering an effective amount of an antimicrobial agent to the animal. In an embodiment, the antimicrobial agent is administered simultaneously with the saponin containing composition. In an embodiment, the anti-microbial agent is selected from the group consisting of sodium chlorate and potassium chlorate. In an embodiment, the anti-microbial agent contains a chlorate group. In an embodiment, the anti-microbial agent is sodium chlorate.

In an embodiment, the invention includes a method for reducing protozoa populations in the digestive system of an animal including administering an effective amount of a saponin containing composition to the animal and administering an effective amount of an anti-microbial agent to the animal. In an embodiment, the animal is selected from the group consisting of cows, sheep, goats, pigs, and chickens. In an embodiment, the method includes reducing protozoa populations in the rumen of an animal. In an embodiment, the animal is a ruminant. In an embodiment, the animal is *Bos taurus*. In an embodiment, the saponin containing composition includes a plant extract. In an embodiment, the saponin containing composition includes *Yucca, Agave*, or *Quillaja* extract. In an embodiment, the saponin containing composition including *Yucca* extract. In an embodiment, the saponin containing composition includes at least 0.5% by weight of saponins. In an embodiment, the saponin containing composition includes at least 2.0% by weight of saponins. In an embodiment, the antimicrobial agent is administered simultaneously with the saponin containing composition. In an embodiment, the anti-microbial agent is selected from the group consisting of sodium chlorate and potassium chlorate. In an embodiment, the anti-microbial agent contains a chlorate group. In an embodiment, the anti-microbial agent is sodium chlorate.

All publications and patent applications in this specification are indicative of the level of ordinary skill in the art to which this invention pertains. The invention has been described with reference to various specific and preferred embodiments and techniques. However, it should be understood that many variations and modifications may be made while remaining within the spirit and scope of the invention.

We claim:

1. A composition for reducing the bacterial load in the digestive tract of an animal comprising:
   a saponin containing composition comprising *Yucca* extract; and
   an anti-microbial agent comprising sodium chlorate.
2. The composition of claim 1, the saponin containing composition comprising at least 0.5% by weight of saponins.
3. The composition of claim 1, the saponin containing composition comprising at least 2.0% by weight of saponins.
4. The composition of claim 1, wherein the composition is a liquid.
5. The composition of claim 4, the composition further comprising a liquid carrier.
6. The composition of claim 1, wherein the composition is a dry powder.

* * * * *